United States Patent
Österdahl et al.

(10) Patent No.: US 6,791,005 B2
(45) Date of Patent: Sep. 14, 2004

(54) ABSORBENT ARTICLES WITH IMPROVED LEAKAGE SAFETY

(75) Inventors: Eje Österdahl, Västra Frölunda (SE); Åsa Johansson, Göteborg (SE); Ulrika Husmark, Mölnlycke (SE); Ingrid Gustafson, Åsa (SE); Anna Stoltze, Göteborg (SE)

(73) Assignee: SCA Hygiene Products AB, Gothenburg (SE)

( * ) Notice: Subject to any disclaimer, the term of this patent is extended or adjusted under 35 U.S.C. 154(b) by 0 days.

(21) Appl. No.: 10/003,264

(22) Filed: Dec. 6, 2001

(65) Prior Publication Data

US 2002/0087138 A1 Jul. 4, 2002

Related U.S. Application Data

(60) Provisional application No. 60/251,874, filed on Dec. 8, 2000.

(30) Foreign Application Priority Data

Dec. 8, 2000 (SE) .............................................. 0004538

(51) Int. Cl.[7] .............................................. A61F 13/15
(52) U.S. Cl. .................................. 604/378; 604/385.17
(58) Field of Search ................................ 604/378, 379, 604/385.01, 385.17

(56) References Cited

U.S. PATENT DOCUMENTS

| | | | | |
|---|---|---|---|---|
| 4,631,062 A | * | 12/1986 | Lassen et al. | 604/385.02 |
| 4,673,403 A | * | 6/1987 | Lassen et al. | 604/385.17 |
| 4,804,380 A | | 2/1989 | Lassen et al. | |
| 5,382,245 A | * | 1/1995 | Thompson et al. | 604/367 |
| 5,545,156 A | * | 8/1996 | DiPalma et al. | 604/385.23 |
| 5,662,633 A | * | 9/1997 | Doak et al. | 604/378 |
| 6,191,340 B1 | * | 2/2001 | Carlucci et al. | 604/369 |
| 6,198,019 B1 | * | 3/2001 | Hansson et al. | 604/378 |
| 6,392,117 B1 | * | 5/2002 | Mayer et al. | 604/378 |
| 6,455,114 B1 | * | 9/2002 | Goldhirsch et al. | 428/34.7 |
| 6,475,199 B1 | * | 11/2002 | Gann et al. | 604/385.01 |
| 6,492,574 B1 | * | 12/2002 | Chen et al. | 604/378 |
| 2002/0065497 A1 | * | 5/2002 | Kolby-Falk | 604/368 |
| 2002/0082576 A1 | * | 6/2002 | Hansson et al. | 604/381 |

FOREIGN PATENT DOCUMENTS

| | | |
|---|---|---|
| EP | 0 768 072 A1 | 4/1997 |
| WO | WO 95/00095 | 1/1995 |

* cited by examiner

Primary Examiner—Weilun Lo
Assistant Examiner—Michael G. Bogart
(74) Attorney, Agent, or Firm—Young & Thompson

(57) ABSTRACT

An absorbent article, such as a sanitary napkin, a panty liner or a female incontinence napkin, is intended to be carried in the crotch part of the wearer inside her underwear, has a generally elongate shape and includes two long sides, two short sides, two end-portions, a center portion located between the end-portions, a liquid-permeable casing sheet that is intended to lie proximal to the wearer's body in use, a liquid-impermeable casing sheet that is intended to lie distal form the wearer's body in use, and further includes between the layers, as seen in a direction from the liquid-permeable casing sheet towards the liquid-impermeable casing sheet, a drainage layer, an absorption layer, and a hump-forming element which forms together with the drainage layer and the absorption layer a hump that projects out from the plane of the napkin on that side of the napkin which is intended to lie proximal to the wearer in the use. In one embodiment, at least one cut is made through the drainage sheet and the absorption layer, and the hump-forming element is pushed up through these layers.

19 Claims, 4 Drawing Sheets

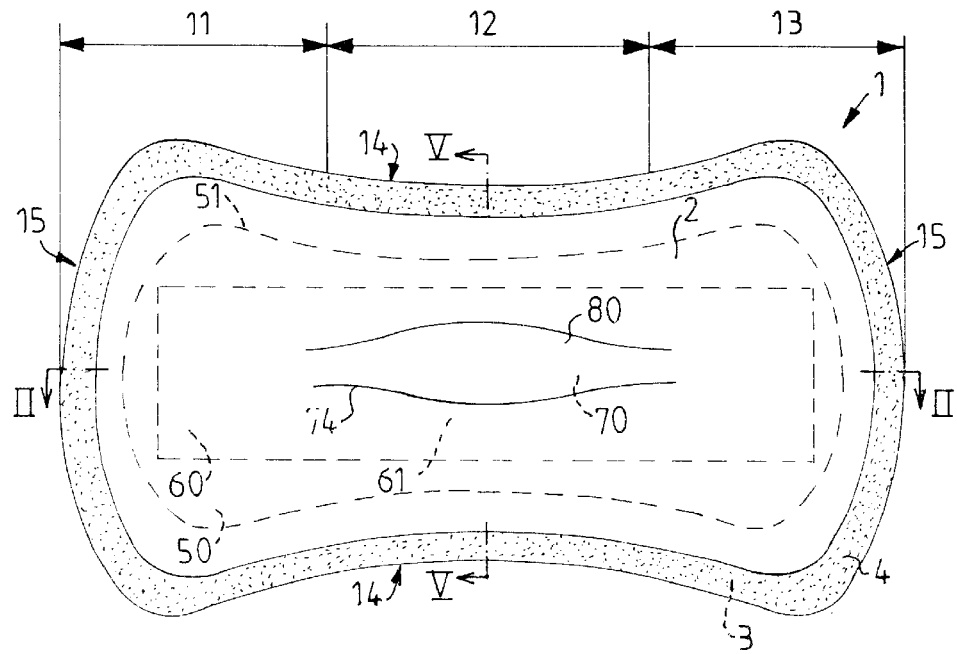
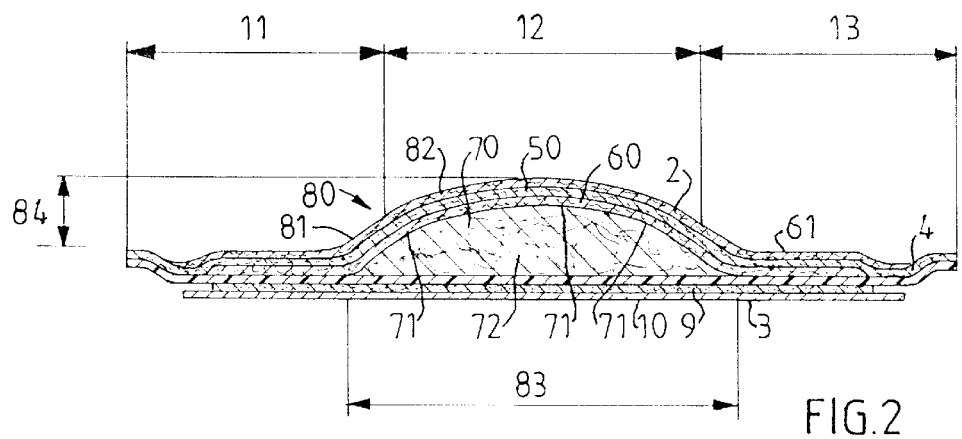

ABSORBENT ARTICLES WITH IMPROVED
LEAKAGE SAFETY

This application claims the benefit of U.S. Provisional Application No. 60/251,874, filed Dec. 8, 2000.

FIELD OF INVENTION

The present invention relates to an absorbent article, such as a sanitary napkin, a panty liner or an incontinence protector, which is intended to be carried in the crotch region of the wearer inside the wearer's panties or pants, said article having a generally elongated shape with two long sides, two short sides, two end-portions, a central portion located between the end-portions, a liquid-permeable casing sheet or top sheet which is intended to lie proximal to the wearer's body in use, a liquid-impermeable casing sheet or backing sheet intended to lie distal from the wearer's body in use, and between said sheets a drainage sheet and an element which forms a hump on the side of the article that lies proximal to the wearer's body in use, as seen in a direction from the liquid-permeable casing sheet towards the liquid-impermeable casing sheet.

BACKGROUND OF THE INVENTION

Conventional absorbent articles of the aforesaid kind are generally flat. Consequently, when the lower abdomen of the female carrier is not flat problems can occur when donning and wearing such articles. In such cases, abutment of the article with the wearer's body is not of the best and if gaps occur between product and the user's body there is a serious risk that body fluid will leak past the long side-edges of the article. Such leakage is particularly undesirable, since it is very liable to soil the wearer's clothes. Rearward leakage is a particular problem in this respect, which normally occurs when the user lies down, for instance at night.

With the intention of solving this problem, it has been proposed to provide the absorbent articles with a pre-formed hump. Absorbent articles that include humps are described in EP-A-0 419 434, among others. The intention of providing absorbent articles with pre-formed humps is to create contact with the genitals of the wearer in use. Discharged body fluids can be caught immediately on leaving the wearer's body and will be absorbed immediately by the article, without running out over its surface and over the long edges of the article.

Another drawback with flat articles is that when the article is used, it is influenced by forces exerted by the wearer's thighs for instance, so as to wrinkle the product and/or cause the long edges of the product to fold over the liquid-permeable surface thereof. A wrinkled surface and/or inwardly folded long edges of the product will significantly reduce the liquid-permeable surface and in many cases to a size that is insufficient to capture all liquid discharged by the wearer at one time, wherewith leakage may occur.

A conventional way of creating a hump is simply to provide a large amount of absorbent material in the absorbent pad within the area where the hump is desired, and form the hump from this excess material. Humps are most often formed from an absorbent material referred to as cellulose fluff pulp, in other words defibred pulp from, e.g., thermo-mechanical pulp, chemithermomechanical pulp, or chemical sulphite pulp or sulphate pulp. Such a material, however, is not stable when wet, and consequently a hump comprised of such material will collapse and lose its shape when wet. In order to obtain a hump consisting of cellulose fluff pulp and having sufficient height whilst the article is in use, it is necessary to use so much cellulose fluff pulp in the production of the hump as to cause the hump to be felt uncomfortable by the wearer. Another problem that occurs with an article constructed in accordance with the above description is that control of the liquid dispersion capacity of the article in the z-direction is lost, because the article loses its shape when wetted. It is also known to produce an article which includes a hump that faces towards the wearer, by placing a moulding or shaping element on top of the absorbent core. One drawback in this respect is that the hump results in inertia in liquid transportation down into the product, due to the fact that the shaping element must be filled with liquid before it releases the liquid to the underlying absorption core, said core having a strong liquid suction and absorbing effect and also a liquid retaining absorption effect. Earlier patent documents have also proposed the use of foam material in providing the hump. A problem with the use of foam material in the hump resides in the difficulties in achieving a foam structure that has sufficiently open pores to obtain effective ingress of liquid into the structure, at the same time as the material shall have great ability in retaining the liquid in its structure without liquid being forced therefrom when subjected to load by the wearer, for instance when the wearer sits down. A hump can also be provided on the upper side of the article, by providing a planar article with a shaping element that takes a convex shape in relation to the wearer when the sides of the article in the region of the crotch are subjected to greater loads from the wearer's thighs. The drawback with this solution is that the shaping element returns to its original planar state immediately the wearer does not subject the sides of the article to pressure, e.g. when she stands with her legs apart or sits in a "lotus position", and also because it is difficult to produce a shape that corresponds essentially to the body shape of the wearer, solely by flexural deformation.

An absorbent article of the kind described in the introduction is known from EP-A1-0 768 072. However, in this case, the hump-forming element also constitutes the element that shall absorb and store discharged liquid and comprises a compressible, resilient and wet-stable material.

The object of the present invention is to provide an absorbent article of the aforesaid kind which conforms well to the wearer's body, makes the risk of leakage slight, and enables the hump-forming element to be manufactured from both absorbent material that is not wet-stable and non-absorbent material.

SUMMARY OF THE INVENTION

This object is achieved in accordance with the invention with an article of the kind described in the introduction that is characterised by an absorbent layer disposed between the drainage layer and the hump-forming element, wherewith the absorbent layer has smaller capillaries than the drainage layer and that part of the hump-forming element that lies against the absorbent layer.

The drainage layer, which has a lower density and therewith larger capillaries than the underlying absorbent layer, is placed on top of the absorbent layer, therewith contributing towards the rapid ingress of liquid in the z-direction down to the absorbent layer, in other words there is obtained a capillary size gradient with large capillaries in the drainage layer and smaller capillaries in the absorbent layer, meaning that the absorbent layer will leach/draw liquid out from the drainage layer. As a result of the difference in the size of the capillaries between the absorbent layer material and the material of the hump-forming element (the absorbent layer has smaller capillaries than the hump-forming material) no natural dispersion of liquid to the underlying hump-forming element will take place, since the capillary forces act in the opposite direction, i.e. the absorbent layer leaches out any liquid present in the hump-forming element. This means that the hump-forming element need not necessarily include material that retains its shape in a wet state, as this element will not be subjected to large amounts of liquid. The construction of the article in this manner makes accessible a wide selection of hydrophobic materials, hydrophilic materials or mixtures thereof for use as hump-forming elements.

The absorbent layer may conveniently extend beyond the contour line of the hump-forming element, but inwardly of the contour line of the drainage layer. The drainage layer is placed on top of the absorbent layer because rapid ingress of the liquid into the hump is desired, wherewith the surface that lies proximal to the wearer in use will be drier and more comfortable than might otherwise be the case, and also results in a softer and more comfortable hump. The advantage gained by virtue of the surface of the absorbent layer being larger than the hump-forming element is that the layer can be draped over the hump-forming element and therewith together create a hump on the upper side of the article while creating an absorbent fluid receiving area around the hump base for dealing with liquid that is too fast to be absorbed on the top of the hump but runs down towards the hump base. There is thus created a safety zone around the hump.

According to one particularly preferred embodiment of the invention, the hump has an elongate form and narrows in a direction towards the end parts of the article and, when seen from one short side of the article, will preferably have a triangular cross-section with a larger width at the base than at the top, preferably with a length of between 20 mm and 140 mm and a height between 5–20 mm. It has been found that such an embodiment imparts good comfort qualities to the article; the article has a less tangible thickness and is less uncomfortable, and is experienced visually as being smaller and more comfortable to wear. The hump will preferably have a generally triangular cross-section, in other words when seen from one short side of the absorbent article, the hump will have a greater width at its base than at its top, where the top is directed towards the side with the liquid receiving casing sheet and the base directed towards the rear side of the article. One advantage afforded by a hump that has the cross-section described above is that there is achieved good body adaptation, where the top of the hump is able to meet the body between labia without discomfort. The hump-forming element is conveniently comprised of a resilient material, that need not necessarily be absorbent.

According to a first embodiment, the hump-forming element is comprised of a non-absorbent material.

According to another embodiment, the hump-forming element is comprised of an absorbent material.

According to still another embodiment, the hump is disposed essentially in the central part of the article.

According to a preferred embodiment of the invention, the hump-forming element extends also over large parts of the end-portions of the article, said end-portions being turned rearwards when the article is used, which results in a corresponding, longitudinally extending hump that projects out from the plane of the article on that side of said article that is intended to lie proximal to the wearer in use.

According to another embodiment, the hump terminates short of the region of the front end-portions of the article, so that the article will conform better to the curvature of the wearer's body. This product is intended to be turned so that the hump will abut the crotch region of the wearer and so that the hump will continue rearwards between the wearer's buttocks, therewith contributing towards effective sealing, primarily when the wearer lies down, for instance to sleep.

According to another preferred embodiment of the invention, the absorption layer and the drainage layer have a longitudinally extending cut along the longitudinal center line of the article, such that the underlying hump-forming element will project up through the absorption layer. Because the hump-forming element will come into contact with moisture during use, it is beneficial for at least that part of the hump-forming element which lies against the overlying absorption layer, i.e. the surface areas of the hump-forming material, to be comprised of a material that has larger capillaries than the absorption layer, and preferably a somewhat retained shape in both dry and wet conditions, and that the portion of the hump-forming element that projects up through the cut in the absorption layer and the drainage layer also has larger capillaries than the drainage layer. This results in an acquisition area that has an extra large capillary structure in the region of the cut up onto the hump. The bordering absorption layer then drains off the acquisition area and disperses the liquid further within the absorption layer. This embodiment is particularly favourable in those cases when a large volume of liquid is discharged within a short period of time.

The longitudinal cut in the absorption layer and the drainage layer also enables the material to be draped more readily around the hump-forming element, therewith facilitating the provision of a more pointed hump apex.

According to still another embodiment of the invention, the absorption layer and the drainage layer include a longitudinal cut in accordance with the aforegoing, wherewith the end parts of the cut have been joined with a further cut that defines between itself and the imaginary extension of the longitudinal cut an angle $\gamma$ corresponding between 10°–90°.

In one variant of the above-mentioned embodiments that include a longitudinal cut in the absorption body and the drainage layer, the density of the hump-forming element increases successively downwards, i.e. away from the absorption layer in a direction towards the liquid-impermeable casing sheet. There is obtained in this way an acquisition area of extra large pore stricture in the region of the cut up on the hump, and part of the liquid will be drained out by the bordering absorption layer and dispersed further within said absorption layer, while part of the liquid will be dispersed and stored within the hump-forming element. Such an embodiment is particularly appropriate when large volumes of liquid are expected to be discharged instantaneously.

BRIEF DESCRIPTION OF THE DRAWINGS

The invention will now be described with reference to the accompanying drawings, in which FIG. 1 is a plan view of a sanitary napkin according to a first embodiment of the invention, seen from the side that lies proximal to the wearer in use;

FIG. 2 is a longitudinal section view of the sanitary napkin in FIG. 1, taken on the line II—II in said Figure;

DESCRIPTION OF EXEMPLIFYING EMBODIMENTS

Figure 3:
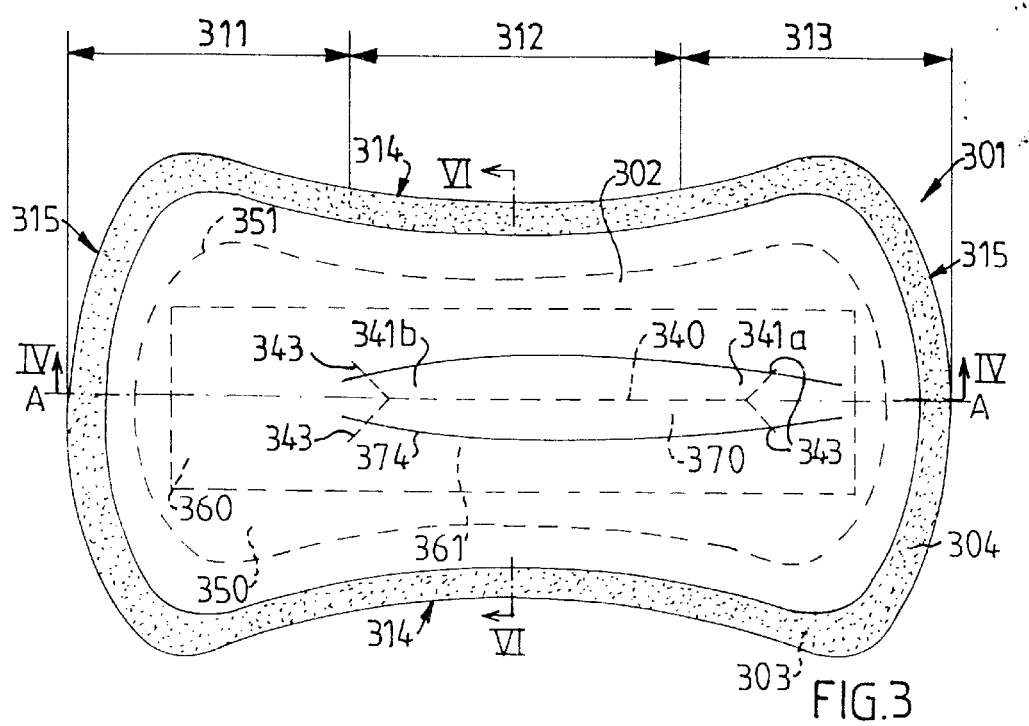
FIG. 3 is a plan view of a sanitary napkin according to a second embodiment of the invention, seen from the side that lies proximal to the wearer in use.

Although absorbent articles in the form of a sanitary napkin are described in the following exemplifying embodiments, it will be understood that these embodiments can also apply to a panty liner or female incontinence napkin. FIG. 1 illustrates a sanitary napkin 1 that has a generally elongate shape, with a longitudinal direction, a transversal direction, two long sides 14, two short sides 15, two end-portions 11, 13 and a central portion 12 located between said end-portions.

Figure 5:
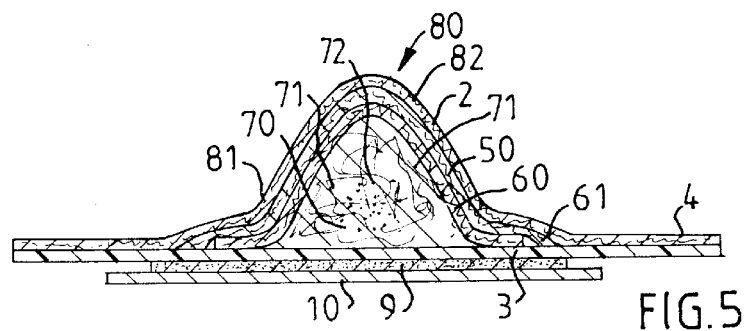
FIG. 5 is a cross-sectional view of the sanitary napkin in FIG. 1, taken on the line V—V in said Figure.

The sanitary napkin 1 shown in FIGS. 1, 2 and 5 includes a liquid-permeable casing sheet or top sheet 2 disposed on that side of the napkin 1 which is intended to lie proximal to the wearer in use. The liquid-permeable casing sheet 2 will conveniently consist in a somewhat soft, skin-friendly material. Different types of non-woven material are examples of suitable liquid-permeable materials. Other casing sheet materials that can be used are perforated plastic films, net, knitted, crocheted or woven textiles, and combinations and laminates of the aforesaid types of material.

The sanitary napkin 1 also includes a liquid-impermeable casing sheet or backing sheet 3, disposed on that side of the napkin 1 distal from the wearer in use. The liquid-impermeable casing sheet 3 is conventionally comprised of thin plastic film. Alternatively, there may be used a liquid-permeable material that has been rendered impermeable to liquid in some way or another. For instance, the liquid-permeable material may be coated with a glue that is impermeable to liquid, and the liquid-permeable layer laminated with a liquid-impermeable material, or hot-calendering a material that was initially liquid-permeable, such as to melt down the surface of the material and therewith obtain a liquid-impermeable layer. Alternatively, there may be used other textiles comprised of hydrophobic fibres and so impervious as to enable them to be used as a liquid barrier layer. The liquid-impermeable casing sheet 3 may beneficially be vapour permeable.

The two casing sheets 2, 3 form a joining edge 4 that projects outwardly around the napkin contour line, and are mutually joined at this edge. The sheets may be joined together by means of any appropriate conventional technique, such as gluing, welding or sewing.

A drainage layer 50, absorption layer 60, and a hump-forming element 70 are disposed between the casing sheets 2, 3 as seen in a direction from the liquid-permeable casing sheet 2 towards the liquid-impermeable casing sheet 3. The absorption layer 60 extends beyond at least a part of a contour line 74 of the hump-forming element 70 but inwardly of a contour line 51 of the drainage layer 50.

The hump-forming element 70 forms together with the casing sheet 2, the drainage sheet 50 and the absorption layer 60 a central hump 80 that projects up from the plane of the napkin on that side of the napkin intended to lie proximal to the wearer in use. The central hump 80 is intended to lie against the wearer's body. The central hump 80 may have an elongate shape and may conveniently narrow or taper in a direction towards the end-portions 11, 13 of the napkin. The hump 80 has a generally triangular cross-section. In other words, when seen from one short side of the absorbent article, the hump has a greater width at the base 81 than at the top 82. The hump will preferably have a length 83 of between 20 mm and 140 mm, and a height 84 of between 5–20 mm.

The hump-forming element 70 is comprised at least partially of a pressure yieldable material, preferably a resilient material, although not necessarily an absorbent material. At least that part of the surface 71 of the hump-forming element that lies against the overlying absorption layer 60 has larger capillaries than the absorption layer or sheet 60. Because of the difference in capillary size between the absorbent layer 60 and the surface 71 of the hump-forming element 70 that lies against the absorption layer 60 (the absorption layer 60 has smaller capillaries than the material of the hump-forming element 70), there is no natural dispersion of liquid from the absorption layer 60 to the underlying hump-forming element 70 before the absorption layer reaches saturation. This means that the hump-forming element need not necessarily be made of a material that retains its shape when wet. The hump-forming element 70 can be made of a material that has an absorbent or non-absorbent structure, cellulose pulp of absorbent or non-absorbent, natural or synthetic fibres, foamed material, or mixtures of these materials. Fibres that can be used to advantage are cellulose fibres of CTMP (chemothermomechanical pulp) or CP (chemical pulp) quality, cotton, rayon, polypropylene fibres (PP), polyethylene fibres (PE). A drainage layer 50 is disposed on top of the absorbent layer 60, so as to obtain rapid liquid passage down to the absorbent layer 60. This drainage layer shall conveniently disperse received liquid in the z-direction, i.e. a direction normal to the plane of the napkin. This material may be an air-laid material that has a lower density, and therewith larger capillaries, than the underlying absorption layer 60. The casing sheet 2 shall have openings that are sufficiently large to allow liquid to be transported down to underlying layers without hindrance.

The drainage layer 50 of the FIG. 1 embodiment is wider and longer than the absorption layer 60 and conveniently follows the outer contour of the periphery on the absorbent product inwardly of the joining region 4 between the two casing sheets 2, 3. This creates an absorption acquisition area 61 around the hump base 81 as a safety zone in the event that there is insufficient time for liquid to be absorbed at the top 82 of the hump 80. This non-absorbed liquid would then run down towards the base 81 of the hump 80 and there be absorbed in the safety area 61.

Material suited for the drainage layer 50 is dry-defibred cellulose admixed with an adhesive type binder, or bonding fibres, tissue material, or non-woven material having a capillary size that is in accord with the above reasoning.

The absorption layer 60 placed beneath the drainage layer 50 and draped over the hump-forming element 70 shall constitute the layer capable of receiving and storing essentially all liquid discharged by the wearer. The absorption layer has smaller capillaries than the overlying drainage layer 50 and the underlying hump-forming element 70. The absorption layer 60 may, for instance, be produced from cellulose pulp. This pulp may exist in rolls, bales or sheets that are dry-defibred and converted in a fluffed state to a pulp mat, sometimes with an admixture of superabsorbents, which are polymers capable of absorbing several times their own weight of water or body liquid (fluid). Examples of other usable materials are different types of foamed materials known, for instance, from SE 9903070-2, natural fibres, such as cotton fibres, peat, or the like. It is, of course, also possible to use absorbent synthetic fibres, or mixtures of natural fibres and synthetic fibres. Patent Application SE 9903070-2 describes a compressed foam material of regenerated cellulose, e.g. viscose. Such foam material will preferably have a density of 0.1 to 2.0 $g/cm^3$. The absorbent material may also contain other components, such as foam-stabilising means, liquid-dispersing means, or a binder, such as thermoplastic fibres, for instance, which have been heat-treated to hold short fibres and particles together so as to form a coherent unit. A suitable material for the absorbent layer 60 according to the invention is the absorbent material described in WO 94/10956. This material is a dry-formed fibre layer of high density and stiffness. In this case, the density will preferably be between 100–300 $g/m^3$ and preferably between 200–250 $g/m^3$. This material can be used directly in an absorbent article, without being first defibred. WO 94/10953 describes another, similar material that has particularly suitable properties for blood absorption purposes.

A fastener means 9 in the form of an elongate rectangular region of self-adhesive is provided on the surface of the liquid-impermeable casing sheet 3 that lies distal from the wearer in use. The fastener means 9 extends over the major part of the liquid-impermeable casing sheet 3. The invention is not restricted to the extension of the fastener means 9, and said means may have the form of elongate stripes, transverse regions, dots, circles, or other patterns and configurations. Neither is the invention restricted to the use of solely adhesive fastener means, since friction fasteners may be used and other types of mechanical fasteners, such as press studs, clips, girdles, pants or the like may be used when found suitable to do so.

When a pressure-sensitive adhesive is used to fasten the sanitary napkin in the panties of the wearer, it is usual to cover the adhesive with a removable protective layer 10 which has release properties on at least that side which faces towards the adhesive medium, so as to protect the adhesive against dirt and also to prevent the adhesive from adhering to other, undesired surfaces or against itself until the napkin shall be used.

Figure 4:
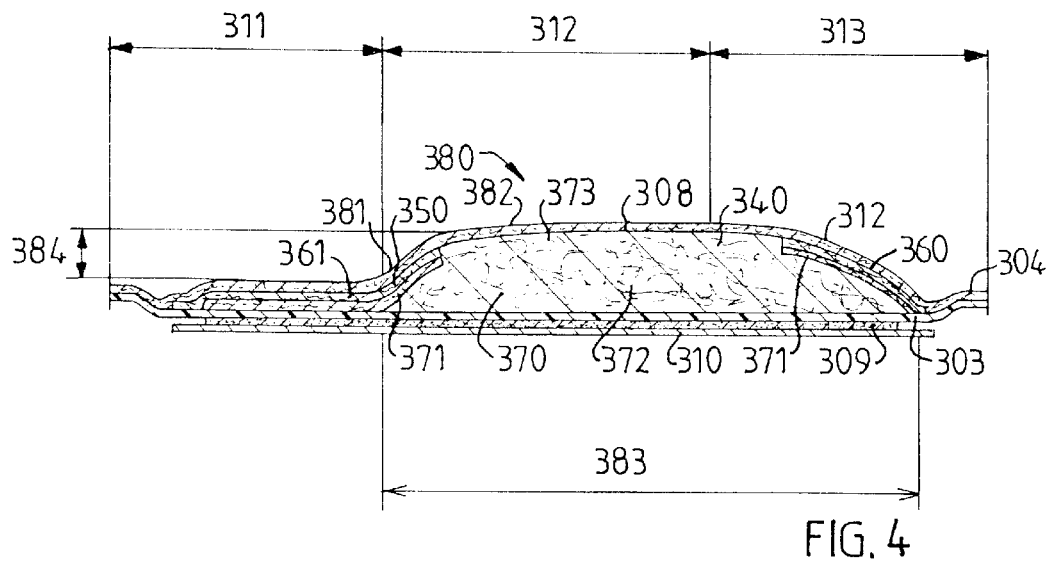
FIG. 4 is a longitudinal sectioned view of the sanitary napkin in FIG. 3, taken on the line IV—IV in said Figure.
Figure 6:
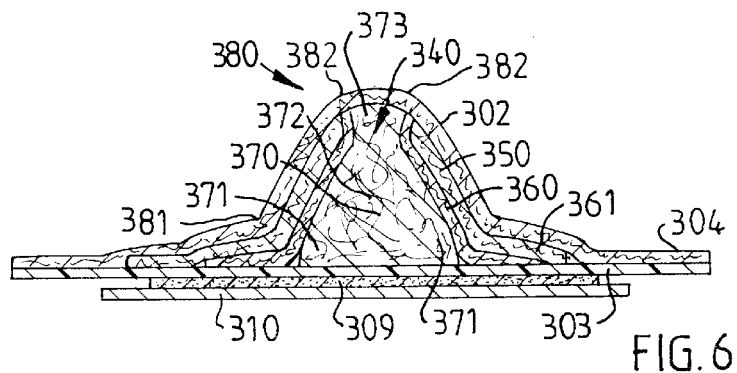
FIG. 6 is a cross-sectional view of the sanitary napkin in FIG. 3, taken on the line VI—VI in said Figure, and illustrates a first hump variant.

FIGS. 3, 4 and 6 illustrate a sanitary napkin 301 of substantially the same design as the sanitary napkin 1 shown in FIGS. 1, 2 and 5. The numbering of the various components of the napkin shown in FIGS. 3, 4 and 6 is therefore analogous with the numbering used in the description of the napkin shown in FIGS. 1, 2 and 5, although with the addition of 300. The napkin 301 shown in FIG. 3, however, differs in two respects from the napkin 1 described with reference to FIG. 1. The hump-forming element 370 also extends over large parts of the rear end-portions 313 of the end parts of the product, resulting in a corresponding, elongate hump 380 that projects out from the plane of the napkin on that side of the napkin which is intended to lie proximal to the wearer in use. It is particularly beneficial for the end-portions 311 placed over the mons veneris of the wearer to be free from the hump 380 when the napkin shall conform better to the curvature of the wearer's body. The napkin 301 is intended to be turned with respect to the wearer so that the hump will lie against the crotch region of the wearer and so that the hump will continue rearwardly between the wearer's buttocks and therewith contribute towards effective sealing, above all when the wearer lies down, for instance to sleep.

The other main difference is that the absorption layer 360 and the drainage layer 350 are provided with a longitudinal cut 340 which extends along the longitudinal center line A—A of the napkin and through which underlying material in the hump-forming element 370 has been pushed up through the two layers of material, the drainage layer 350 and the absorption layer 360. The length of the cut 340 is at least 20 mm. The length of the cut 340 may be at least 20 mm but is preferably not longer than the length of the hump-forming element 370. That part 373 of the hump-forming element that is pushed up through the cut 340 conveniently has larger capillaries than the drainage layer. There is obtained in this way an acquisition surface which presents large liquid receiving spaces that result in quicker acquisition of the liquid into the napkin, which is beneficial particularly in certain cases when large volumes of liquid are liable to be discharged over a short period of time. It is beneficial when that part 373 of the hump-forming element pushed up through the absorption layer 360 and the drainage layer 350 includes a material which will not bind liquid (fluid) firmly to its fibres, but that will conduct the liquid (fluid) further to the absorption layer 360, so that no liquid will remain close to the liquid-permeable casing sheet 302 and therewith contribute towards a wet surface against the wearer's skin. Fibres that can be considered suitable for this part 373 of the hump-forming element 370 are non-absorbent synthetic fibres and absorbent fibres that have been rendered hydrophobic and therefore are no longer absorbent.

The provision of a longitudinally extending cut 340 in the drainage layer 350 and the absorption layer 360 enables the triangular profile of the hump 380 to be retained more easily, even when the hump is subjected to load from the wearer's body. In the illustrated embodiment, the cut 340 is made without removing material from the drainage layer 350 and the absorption layer 360, which is preferred. The cut can, of course, also be provided by forming a cut-out in the sheets 350, 360, although this complicates manufacture and is therefore not preferred.

Figure 7:
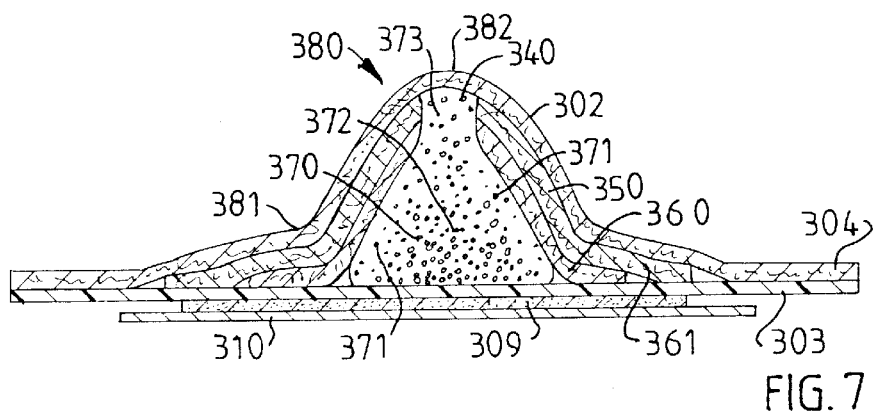
FIG. 7 is a cross-sectional view similar to that of FIG. 6 and shows a second hump variant according to the second embodiment of the invention.

FIG. 7 illustrates a variant of the hump 380 in the second embodiment, in which the density of the hump-forming element 370 increases successively downwards away from the absorbent layer 360 and towards the liquid-impermeable casing sheet 303. The sparsely drawn dots in FIG. 7 are intended to illustrate low density and therewith large capillary sizes, while the more tightly packed dots are intended to show successively higher densities and therewith successively smaller capillaries. There is obtained in this way an acquisition area that has an extra large core structure in the region of the cut 340 up to the peak 380 of the hump, wherewith some of the liquid can be drained out and further dispersed by the bordering absorption layer 360, at the same time as some of the liquid is dispersed and stored within the hump-forming element 370. The description of the hump made earlier with reference to FIGS. 3, 4 and 6 also applies to the hump 380 of the FIG. 7 embodiment, in other words it is beneficial for that part 373 of the hump-forming element which projects up through the absorption layer 360 and the drainage layer 350 to include material that will not bind liquid firmly to its fibres but will lead the liquid further to the absorption layer 360, so that no liquid will remain close to the liquid-permeable casing sheet 302 that might otherwise contribute towards a wet surface against the wearer's skin. It is desirable that at least the central part 372 of the hump-forming element is shape-stable in both a dry and a wet state. The hump-forming element according to the embodiments shown in FIGS. 3–4, 6 and 7 may, e.g., be comprised of an absorbent structure, cellulose pulp comprised of absorbent or non-absorbent natural or synthetic fibres, foamed material, or mixtures of these materials. Those fibres that can be used beneficially are cellulose fibres of CTMP or CP quality, cotton, rayon, PP fibres, PE fibres, synthetic fibres whose surfaces have been made hydrophilic. The aforedescribed structures, fibres and mixtures may also contain particles of superabsorbent material evenly distributed in the fibre structure or laid in layers. By superabsorbent material is meant polymers that exist in the form of fibres, flakes, particles, granulates or the like and which are able to absorb several times their own weight of body fluid whilst swelling and forming a gel. Different densities can be obtained in the hump-forming element 370, by mat-forming said element for instance, i.e. by delivering a stream of the fibre material in question and air into a mould that includes evacuation holes in a number of levels, whereafter the air is evacuated and parts of the formed hump-forming element 370 therebetween are compressed to respective desired densities. Alternatively, layers of mutually different densities may be combined.

Figure 8:
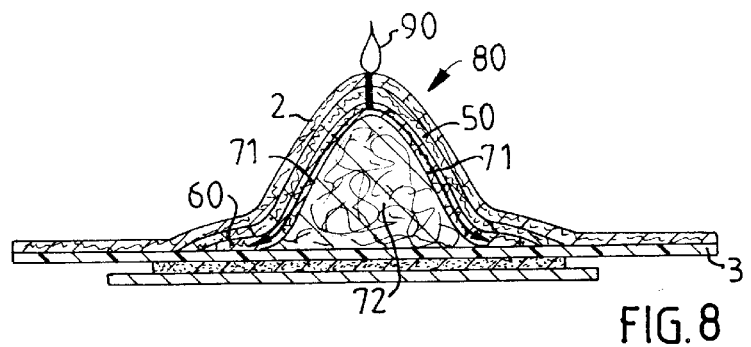
FIG. 8 is a cross-sectional view similar to that of FIG. 5, wherewith the dispersion of liquid in the hump has been drawn schematically.
Figure 9:
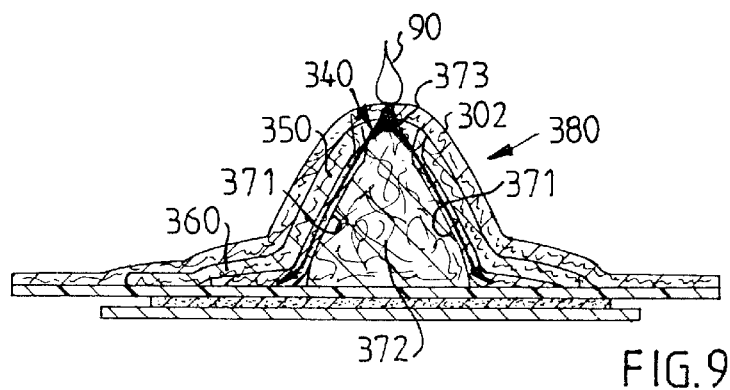
FIG. 9 is a cross-sectional view similar to that of FIG. 6, where dispersion of liquid in the hump according to the first variant has been drawn schematically.
Figure 10:
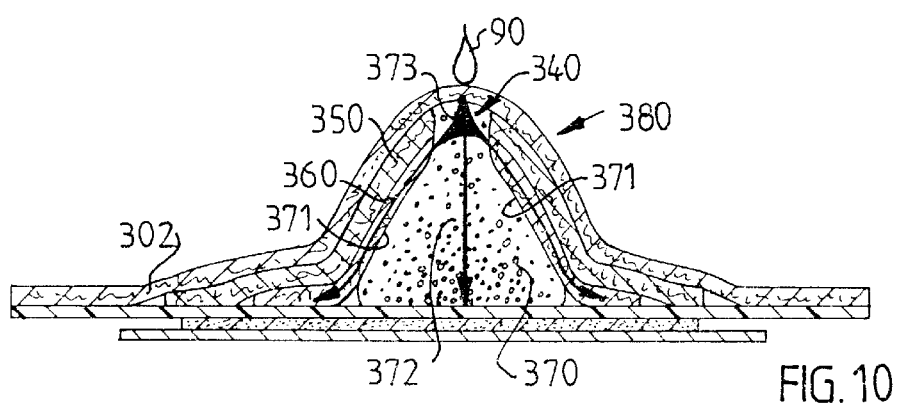
FIG. 10 is a cross-sectional view similar to that of FIG. 7 showing the second variant of the hump according to the second embodiment of the invention, where dispersion of liquid in the hump has been drawn schematically.

FIGS. 8–10 illustrate schematically the general disbursement of the liquid down into the napkin, depending on the variant of a hump-forming element chosen for use in the different embodiments.

FIG. 8 illustrates a hump which lacks a cut through the drainage layer 50 and the absorption layer 60. At least the surface 71 of the hump-forming element that lies against the absorption layer 60 shall have a capillary size that is larger than the capillary size of the absorption layer 60. The central part 72 of the hump-forming element may have a capillary size that is smaller, greater than or the same as the surface 71 of the hump-forming element that lies against the absorption layer 60. The liquid 90 is absorbed in the z-direction through the casing sheet 2 and the drainage layer 50, down to the underlying absorption layer 60 where the liquid is further dispersed and stored therein.

FIG. 9 illustrates a hump that includes a cut 340 through the drainage layer 350 and the absorption layer 360. The surface 371 of the hump-forming element that lies against the absorption layer 360 and that part 373 of the hump-forming element which projects up through the drainage layer 350 and the absorption layer 360 shall at least have a capillary size that is greater than that of the absorption layer 360. The central part 372 of the hump-forming element may have a capillary size that is smaller or greater than or the same as the capillary size of the surface 371 of the hump-forming element that lies against the absorption layer 360. The liquid 90 is absorbed in the z-direction through the casing sheet 302 and down into that part of the hump-forming element 373 that has been pushed up through the cut 340, and from there down to the underlying absorption layer 360, where the liquid is further dispersed in said layer and stored therein.

FIG. 10 illustrates a hump that includes a cut 340 through the drainage layer 350 and the absorption layer 360. The surface 371 of the hump-forming element that lies against the absorption layer 360 and that part 373 of the hump-forming element 370 that projects up through the drainage layer 350 and the absorption layer 360 shall at least have a capillary size that is greater than that of the absorption layer. The size of the capillaries in the central part 372 of the hump-forming element decreases gradually in a direction towards the liquid-impermeable casing sheet 3, so as to form a natural absorption gradient down in the central part 372 of the hump-forming element. The liquid 90 is absorbed in the z-direction through the casing sheet 302 down into that part 373 of the hump-forming element 370 that has been pushed up through the cut 340, and from there down to the underlying absorption layer 360 where some of the liquid is dispersed further in said layer 360 and stored therein. Moreover, owing to the capillary size gradient, some of the liquid may be dispersed downwards and into the central part 372 of the hump-forming element.

Figure 11:
FIGS. 11 and 12 show examples of cuts in the drainage layer and the absorption layer.
Figure 12:
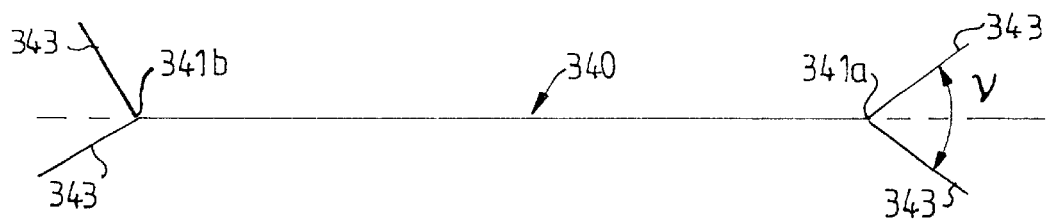

FIGS. 11 and 12 illustrate examples of the appearance of a cut 340. The length of the cut will suitably be at least 20 mm and preferably not greater than the length of the hump-forming element 370; see FIG. 3. The cut 340 may consist solely in a simple longitudinally extending cut, as shown in FIG. 11, or a cut such as that described in FIG. 12. It has been found beneficial to join the end-portions 341a, 341b of the longitudinally extending cut (see FIG. 12) with further cuts 343 that define between themselves and the imaginary extension of the longitudinal cut 340 an angle γ corresponding to between 10°–90°. This enables the cut 340 to be opened out more easily, so as to enable underlying hump-forming material 370 to be pushed up through the two layers, the drainage layer 350 and the absorption layer 360 more easily. The length of the cuts 343 is between 3–25 mm, preferably between 5–15 mm. It is not necessary for the cuts 343 on respective sides of the longitudinally extending cut 340 to have the same lengths or placements in relation to the longitudinally extending cut 340. Neither is it necessary to form the cuts in the same way at the two end-portions 341a, 341b.

Due to its three-dimensional form adapted to fit the woman body, the article according to the invention is very suitable for carrying an active substance. Examples of suitable active substances are given in WO-A1-99/17813, which is referred to for further details. In WO-A1-99/45099 the use of *Lactobacillus plantarum,* strain LB931, which has been deposited at Deutsche Sammlung von Mikroorganismen, and been assigned accession number DSM11918, in absorbent articles is disclosed. Preferably, LB931 is comprised in the article according to the invention in the area thereof coming in contact with the urogenital region, i.e. perineum, urethra and vagina. The active substance is thus disposed on the area of the article comprising the hump-forming element. The active substance is preferably disposed on the liquid-permeable casing sheet or on the drainage sheet and also on the hump-forming element in the embodiment in which a part thereof projects through the absorbent layer and the drainage layer.

It will be understood that the invention is not restricted to the aforedescribed exemplifying embodiments thereof, and that a number of further variants and modifications are conceivable within the scope of the accompanying claims. Furthermore, all conceivable combinations of the described embodiments are included in the scope of the invention.

For instance, it is, of course, possible to provide the first embodiment according to FIG. 1 with a cut that is similar to the cut described with reference to the embodiment according to FIG. 3, and equally as well to omit said cut from this embodiment.

LIST OF NUMBER REFERENCES IN THE FIGURES 1,301=Sanitary napkin
2,302=Liquid-permeable casing sheet
3,303=Liquid-impermeable casing sheet
4,304=Join between the two casing sheets
9,309=Fastener means
10,310=Protective layer with release properties for the fastener means
11,311=Front end-portions of the napkin
12,312=Center portion of the napkin
13,313=Rear end-portions of the napkin
14,314=Long sides of the napkin
15,315=Short sides of the napkin
50,350=Drainage layer
51,351=Contour line of the drainage layer
60,360=Absorption layer
61,361=Absorbent acquisition area around the base of the hump
70,370=Hump-forming element
71,371=Periphery of the hump-forming element
72,372=Central part of the hump-forming element
73,373=That part of the hump-forming element which is pushed up through the cut
74,373=The contour line of the hump-forming element //74,373???//
80,380=The hump of the sanitary napkin
81,381=The hump base
82,382=The hump peak
85,385=The hump end-portions
84,384=The hump height
83,383=The hump lengths
90=Liquid (fluid)
340=Longitudinal cut
341a=One end-portions region of the longitudinally extending cut
341b=The other end-portions region of the longitudinally extending cut
343=Cuts formed at an angle to the longitudinally extending cut

What is claimed is:

1. An absorbent article intended to be carried in the crotch part of the wearer within the wearer's underclothes, said article having an essentially elongated shape and including two long sides (14), two short sides (15), two end-portions (11, 13), a centre part (12) located between said end-portions, a liquid-permeable casing sheet (2) which is intended to lie proximal to the wearer's body in use, a liquid-impermeable casing sheet (3) which is intended to lie distal from the wearer's body in use, and further includes between said sheets (2; 3) and as seen in a direction away from the liquid-permeable casing sheet (2) towards the liquid-impermeable casing sheet (3), a drainage layer (50) and a hump-forming element (70) which forms a hump (80) on that side of the article which is intended to lie proximal to the wearer's body in use, characterised by an absorption layer (60) disposed between the drainage layer (50) and the hump-forming element (70), said absorption layer (60) having smaller capillaries than the drainage layer (50) and the hump-forming element (70).

2. An absorbent article according to claim 1, characterised in that the absorption layer (60) extends beyond at least a part of a contour line (74) of the hump-forming element (70) but inwardly of a contour line (51) of the drainage layer (50).

3. An absorbent article according to claim 1, characterised in that the hump-forming element (70) is comprised of a pressure yieldable material.

4. An absorbent article according to claim 1, characterised in that the hump-forming element (70) is comprised of a non-absorbent material.

5. An absorbent article according to claim 1, characterised in that the hump-forming element (70) is comprised of an absorbent material.

6. An absorbent article according to claim 1, characterised in that the absorption layer (60) is comprised of a dry-formed sheet which contains 5–100% cellulose fibre and which has a density of between 100–300 $g/m^3$ and a weight per unit area between 30–2000 $g/m^2$, and which sheet has been formed by compressing a web containing cellulose fibres in the absence of subsequent defibration and fluff formation.

7. An absorbent article according to claim 1, characterised in that the absorption layer (60) is comprised of a compressed cellulose foam layer that has a density of between 0.2–2.0 $g/m^3$.

8. An absorbent article according to claim 1, characterised in that the hump (80) has an elongate shape, narrows in a direction towards the end-portion (11, 13) of said article and has a triangular cross-section as seen from one short side of the article, with a larger width at the base (81) than at the peak (82) and with a length (83) of between 20 mm and 140 mm and a height (84) between 5–20 mm.

9. An absorbent article according to claim 8, characterised in that the hump (80) is disposed essentially in the centre part (12) of the article.

10. An absorbent article according to claim 1, characterised in that the rear end-portion (85) of the hump extends into the rear end-portion (13) of said article.

11. An absorbent article according to claim 1, characterised in that the front end-portion (85) of the hump terminates short of the region of the front end portion (11) of the article.

12. An absorbent article according to claim 1, characterised in that the absorption layer (360) and the drainage layer (350) include a longitudinally extending cut (340) along the longitudinally extending center line (V) of the article and through which cut a part of the underlying hump-forming element (370) is pushed up through the absorption layer (360) and the drainage layer 350).

13. An absorbent article according to claim 12, characterised in that the part of the hump-forming element (373) that projects up through the absorption layer (360) and the drainage layer (350) has larger capillaries than the drainage layer (350).

14. An absorbent article according to claim 12, characterised in that the cut (340) shall have a length of at least 20 mm.

15. An absorbent article according to claim 12, characterised in that at least one of the end-portions (341a, 341b) of the longitudinally extending cut are joined with a further cut (343) in the region of the end-portions (341a, 341b) of said longitudinally extending cut, wherein said other cut (343) defines between itself and the imaginary extension of the longitudinal cut (340) an angle γ corresponding to 10°–90°; and in that the other cut (343) has a length of between 3–25 mm.

16. An absorbent article according to claim 1, characterised in that an active substance is disposed on the liquid-permeable casing sheet or the drainage layer in the area thereof comprising the hump-forming element.

17. An absorbent article according to claim 12, characterised in that an active substance is disposed on the liquid-permeable casing sheet or the drainage layer in the area thereof comprising the hump-forming element and/or on the part of the hump-forming element that projects up through the absorption layer and the drainage layer.

18. An absorbent article according to claim 16, characterised in that the active substance is *Lactobacillus plantarum,* strain LB931, which has been deposited at Deutsche Sammlung von Mikroorganismen, and been assigned accession number DSM11918.

19. An absorbent article according to claim 17, characterised in that the active substance is *Lactobacillus plantarum,* strain LB931, which has been deposited at Deutsche Sammlung von Mikroorganismen, and been assigned accession number DSM11918.

* * * * *